United States Patent [19]
Goldstein

[11] 4,396,606
[45] Aug. 2, 1983

[54] NOVEL POLYPEPTIDE ANALGESICS

[75] Inventor: Avram Goldstein, Stanford, Calif.

[73] Assignee: Addiction Research Foundation, Palo Alto, Calif.

[21] Appl. No.: 91,615

[22] Filed: Nov. 5, 1979

[51] Int. Cl.³ .................... A61K 37/00; C07C 103/52
[52] U.S. Cl. ................. 424/177; 260/112.5 R
[58] Field of Search ................. 260/112.5 R; 424/177

[56] References Cited

U.S. PATENT DOCUMENTS

| | | | |
|---|---|---|---|
| Re. 29,842 | 11/1978 | Li | 260/112.5 R |
| 4,097,471 | 6/1978 | Sarantakis et al. | 260/112.5 R |
| 4,098,778 | 7/1978 | Li | 260/112.5 R |
| 4,103,005 | 7/1978 | Li | 260/112.5 R |
| 4,116,950 | 9/1978 | Li | 260/112.5 R |
| 4,123,523 | 10/1978 | Dutta et al. | 260/112.5 R |
| 4,127,525 | 11/1978 | Coy et al. | 260/112.5 R |
| 4,127,526 | 11/1978 | Coy et al. | 260/112.5 R |
| 4,127,527 | 11/1978 | Coy et al. | 260/112.5 R |
| 4,127,528 | 11/1978 | Coy et al. | 260/112.5 R |
| 4,127,538 | 11/1978 | Coy et al. | 260/112.5 R |
| 4,127,540 | 11/1978 | Coy et al. | 260/112.5 R |
| 4,143,032 | 3/1979 | Sarantakis | 260/112.5 R |
| 4,148,788 | 4/1979 | Wang | 424/177 |
| 4,161,522 | 7/1979 | Hamburger | 260/112.5 R |
| 4,178,284 | 12/1979 | Sarantakis | 260/112.5 R |
| 4,180,501 | 12/1979 | Coy et al. | 260/112.5 R |
| 4,207,311 | 6/1980 | Brown et al. | 424/177 |
| 4,223,017 | 9/1980 | Lazarus | 424/177 |
| 4,229,438 | 10/1980 | Fujino et al. | 424/177 |
| 4,230,696 | 10/1980 | Hashim | 424/177 |
| 4,232,008 | 11/1980 | Goldstein | 424/177 |
| 4,250,087 | 2/1981 | Li | 260/112.5 R |
| 4,254,106 | 3/1981 | Wilkinson | 260/112.5 R |
| 4,254,107 | 3/1981 | Veber et al. | 424/177 |
| 4,256,736 | 3/1981 | de Wied et al. | 424/177 |

*Primary Examiner*—Delbert R. Phillips
*Attorney, Agent, or Firm*—Bertram I. Rowland

[57] ABSTRACT

Novel opioid compounds are provided having a phenolic hydroxyl and a pentet of alternating basic hydrophilic and hydrophobic groups derived from basic amino acids and hydrophobic amino acids. Desirably, the pentet, usually sextet, is separated from the phenolic ring by at least about 3 atoms in a chain, preferably at least about 15 atoms in a chain and not more than about 30 atoms in a chain (for rings one will take the average of the shortest and longest distances). Particularly, a polypeptide is provided having tyrosyl at the amine end, desirably as the first amino acid of leu- or met-enkephalin and a sextet of alternating basic hydrophilic and hydrophobic amino acids spaced from the enkephalin by at least about one amino acid. Desirably, the polypeptide is at least 1,200 molecular weight and under about 2,500 molecular weight.

6 Claims, No Drawings

NOVEL POLYPEPTIDE ANALGESICS

BACKGROUND OF THE INVENTION

1. Field of the Invention

The desire to understand the mechanisms by which analgesics effectuate the reduction of pain and to develop new analgesics which are more effective and freer of side effects engendered the discovery of β-endorphin and the smaller polypeptides leu-enkephalin and met-enkephalin. The first five amino acids of β-endorphin are the five amino acids of met-enkephalin. There has been substantial activity in trying to develop modifications of leu-enkephalin and met-enkephalin to enhance their activity, since the activity of the smaller polypeptides is substantially lower than β-endorphin.

Various techniques to inhibit degradation of the polypeptide have involved employing the artificial stereoisomer of one of the amino acids. Also, the carboxy end has been amidified and various amino acids have been added to the ends of the chain to enhance or modify activity.

In developing new polypeptide analgesics, there are a number of important considerations. A desirable analgesic will have relatively few amino acids, so as to be easily and economically synthesized in good yield. Furthermore, it is desirable that the polypeptide analgesic be easily administered and migrate to its natural binding site without substantial degradation. Otherwise, the polypeptide will have to be introduced adjacent to or at the site of binding to achieve the analgesic effect. Desirably, the potency should be substantially higher than available analgesics, while at the same time because of the reduced amount administered or because of its particular structure, the analgesic should be relatively free of undesirable side effects.

With the large number of amino acids available, and, the possibility for modification, such as acetylation and amidification, there are an astronomical number of possibilities of combining amino acids to achieve opioid potency. While leu-enkephalin and met-enkephalin have a tyrosine group which is analogous to the phenolic group of morphine, in view of the small size of morphine and analogous opioids, there were no directions as to how the enkephalins might be extended and, when extended, how their potency might be enhanced or activities modified, except for the β-endorphin sequence. Therefore, while the possibility of having a polypeptide analgesic presented itself, the ability to determine an appropriate structure remained tantalizingly difficult.

2. Brief Description of the Prior Art

Cox et al. (1975) Life Sci. 16 1777 and Lowney et al. (1979) Life Sci. 24 2377 report two pituitary opioid peptides. Kangawa et al. (1979) Biochem. Biophys. Res. Comm. 86, 153 report an opioid peptide from porcine hypothalamus.

SUMMARY OF THE INVENTION

Novel oligopeptides are provided having alternating basic hydrophilic amino acids and hydrophobic amino acids, having at least five units, which oligopeptides are employed as precursors for conjugating to opioid compounds, particularly polypeptide opioids. The oligopeptides are joined by a short chain to a phenolic group, which may be part of a tyrosyl unit or a morphine alkaloid or synthetic mimetic analogs thereof.

Of particular interest is a polypeptude having at the N-terminus a tridecapeptide having at the N-terminus the five amino acid sequence of leu-enkephalin and an octapeptide which includes the alternating sequence.

The subject compounds find use as precursors to analgesics, as analgesics, as opioid agonists and in studying the structure of opioid binding sites. Finally, the subject polypeptides may be combined with acidic polypeptides having reciprocal amino acids to provide substantially neutral salts.

DESCRIPTION OF THE SPECIFIC EMBODIMENTS

In accordance with the subject invention, compounds are provided for use in binding to opioid receptor sites of mammals which involve an oligopeptide pentet, usually sextet, of alternating basic hydrophilic side chains and hydrophobic side chains or hydrogen. The oligopeptide is desirably linked to a phenolic group through a relatively short chain, either an amino acid chain generally having at least one amino acid, usually having from about 3 to 6 amino acids, or by at least about 3 atoms and not more than 18 atoms, the atoms in the chain being C and N, while the linking group comprising the chain and atoms bonded thereto consisting of C, H, N and O, where O is oxy or non-oxo-carbonyl, N is amino or amido and C is aliphatic (includes cycloaliphatic). The oligopeptide may be bonded to compounds having known opioid activity, such as morphine, leu-enkephalin, or met-enkephalin, at a site distant from the phenolic group. The opioid compounds will have molecular weights of at least about 1,200, usually 1,500 and not more than about 2,500. They will generally have from about 4 to 6, usually 5, basic amino acid groups, not more than a total of four basic amino acids linked to another basic amino acid.

For the most part, the oligopeptide will have the following formula.

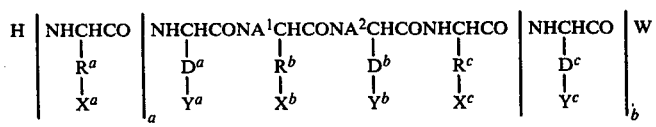

wherein:
one of a and b is 0 or 1 and the other is 1;
all the Rs and Ds are bonds or alkylene groups of from 1 to 6, preferably from 1 to 4, more preferably from 2 to 3 carbon atoms wherein the alkylene groups may be straight or branched chain, usually methylene, polymethylene or (ω-1)methyl-polymethylene with the proviso that the Rs and Ds are alkylene when bonded to other than hydrogen;
either the Xs or the Ys are hydrogen, when other than hydrogen, they are basic nitrogen groups, normally amino, amidinyl or guanidinyl;
with the proviso that when the Xs are hydrogen, $A^1$ may be taken together with $X^b$ or when the Ys are hydrogen, $A^2$ may be taken together with $Y^b$ and the atoms to which they are attached to form a heterocyclic ring of from five to six members, which may be hydroxyl substituted or unsubstituted, normally unsubstituted; $A^1X^b$ or $A^2Y^b$ defining an alkylene or hydroxylkylene chain; when not taken together with $X^b$ or $Y^b$, $A^1$ and $A^2$ are hydrogen; and W is OH, amino or an amino acid or polypeptide of up to about ten, usually up to about four, amino acids, which do not interfere with the opioid properties of the base structure and are joined by a peptide bond.

When the Xs are hydrogen, $R^a$-$X^a$ will be alkyl of from 1 to 5, preferably of from 2 to 3 carbon atoms, more preferably isopropyl;

$R^b$-$X^b$ is alkylene of from 1 to 5, usually of from 2 to 3 carbon atoms and particularly preferred that $R^b$-$X^b$ is taken together with $A^1$ to provide trimethylene or hydroxytrimethylene;

$R^c$-$X^c$ is alkylene of from 1 to 5, more usually of from 2 to 4 carbon atoms, and preferably propyl;

$D^a$-$Y^a$ is a terminal basic substituted alkylene group of from 1 to 5, preferably 2 to 3 carbon atoms, where $Y^a$ is amino or guanidinyl, preferably $D^a$ is alkylene of three carbon atoms and $Y^a$ is guanidinyl;

$D^b$-$Y^b$ is a terminal basic substituted alkylene group of from 1 to 5, more usually of from 2 to 4 carbon atoms, and preferably 4 carbon atoms, and $Y^b$ is amino;

$D^c$-$Y^c$ has the same definition as $D^b$-$Y^b$.

Alternatively, when the Xs are the basic groups and the Ys are hydrogen, the defintions of $R^a$-$X^a$ and $D^a$-$Y^a$ are exchanged;

$R^b$-$X^b$ with $A^1$ then assumes the definition of $D^b$-$Y^b$ with $A^2$; and $R^c$-$X^c$ has the definition of $D^c$-$Y^c$ previously indicated.

(Rather than repeating the above formula, it will henceforth be referred to as Formula 1 and inserted appropriately. Also, unless otherwise indicated, the amino acids referred to are the amino acids natural to man.) A preferred embodiment of Formula 1 is a polypeptide of at least six, preferably seven amino acids, where the polypeptide embodies the amino acids of Formula 1, and has two additional amino acids at the N-terminus, preferably at least one, and more preferably both being basic amino acids and the N-terminus of the Formula 1 oligopeptide is hydrophobic, i.e. $X^a$ is hydrogen.

For the most part, with the Xs being hydrogen, these compounds will have the following formula:

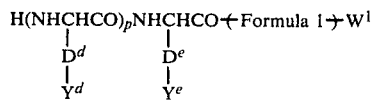

where $D^{d-e}$ are a bond (only when the Y to which the D is bonded is hydrogen) or alkylene groups of from 1 to 6, usually from 2 to 5, preferably from 2 to 4 carbon atoms and $Y^{d-e}$ are hydrogen or a basic nitrogen group e.g., amino, amidinyl or guanidinyl, particularly, $D^{d-e}$ are alkylene of three carbon atoms and at least one of $Y^{d-e}$ is amino or guanidinyl; preferably all the Ys are basic groups;

$W^1$ is hydroxy, amino or an amino acid or polypeptide of up to about 10, usually 4, amino acids bonded by a peptide link to Formula 1; and p is 0 or 1, usually 1, and a and b are preferably 1.

The above formula will be referred to as Formula 2.

Both Formula 1 and Formula 2 may be modified in a number of different ways. One or more, usually not more than 2, and preferably only 1 may be other than the natural L-configuration. Usually, the unnatural D-configuration will be a hydrophobic amino acid, rather than a basic hydrophilic amino acid. Furthermore, the amino groups may be modified by acetylation or nitro- substituted to reduce the basicity of the molecule, or may be employed as mineral acid salts, such as the hydrochlorides.

Either Formula 1 or Formula 2 may be bonded to a compound having opioid activity.

By opioid activity is intended agonist, antagonist and partial agonist activity. Opioid activity is recognized by effectiveness in such common tests as the guinea pig ileum and the vas deferens tests described subsequently. An antagonist is a compound which is not effective in such tests, but is able to block a compound which is effective. A partial agonist is a compound which shows both effects, having some effectiveness in the test, but able to block other effective compounds. In effect, all of these compounds are ligands for an opioid receptor.

Various compounds having opioid activity may be employed, particularly those having a phenolic group or a substituted phenolic group, where the substituent may be removed in vivo. Such compounds include morphine, heroin, codeine, naloxone, levorphanol, nalorphine, naltrexone, leu-enkephalin and met-enkephalin.

The morphine compounds will for the most part have the following formula:

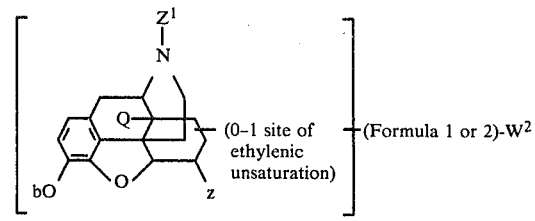

wherein:
one of Z or $Z^1$ is a linking group to Formula 1 or Formula 2 of from 1 to 10, usually 1 to 6 carbon atoms; when not a linking group, Z is hydroxyl and $Z^1$ is an aliphatic group (includes cycloaliphatic) of from 1 to 4, usually 1 to 3, carbon atoms having from 0 to 1 site of ethylenic unsaturation, normally methyl, allyl or cyclopropylmethyl;
b is hydrogen or methyl; and
Q is hydrogen or hydroxyl;
$W^2$ is hydroxyl, amino or an amino acid or polypeptide of not more than about 10, usually 4, amino acids which does not adversely affect the opioid activity of the subject oligopeptides.

The next compositions are those related to enkephalin derivatives, to the extent that the N-terminus has a tyrosyl amino acid. These compounds will for the most part have the following formula:

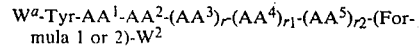

wherein:

Tyr is tyrosine;

AA¹, AA² and AA⁵ are hydrophobic amino acids having hydrogen or a hydrocarbon side chain of from 1 to 8, usually 1 t 4 carbon atoms, and may be either D or L configuration, preferably only one is D configuration, particularly AA¹; preferably, AA¹, AA² and AA⁵ have hydrogen (glycine) or an alkyl group of from 1 to 2 carbon atoms, preferably 1 carbon atom (alanine);

AA³ is a hydrophobic amino acid, normally having a hydrocarbon substituent of from 2 to 8, usually 6 to 8 carbon atoms, particularly phenyl;

AA⁴ is a hydrophobic amino acid of from 3 to 6 carbon atoms normally having a side chain having from 0 to 1 chalcogen heteroatom of atomic number 8 to 16, normally bonded solely to carbon, and is generally alkyl of from 1 to 4 carbon atoms, particularly 4 carbon atoms, alkylthioalkylene or alkoxyalkylene, wherein the alkyl substituent is usually of from 1 to 2 carbon atoms, more usually 1 carbon atom, and the alkylene group is of 1 to 3 carbon atoms, usually 1 to 2 carbon atoms e.g. leucine and methionine;

$r$ and $r^1$ are 0 to 1, usually 1, while $r^2$ is 0 to 1, usually 0;

$W^a$ is H for agonist activity and alkyl or cyclopropylmethyl for antagonist activity; and $W^2$ is hydroxyl, amino or an amino acid or polypeptide of not more than about 10, usually 4, amino acids which does not adversely affect the opioid activity of the subject oligopeptides.

Particular oligopeptides have the following formula:

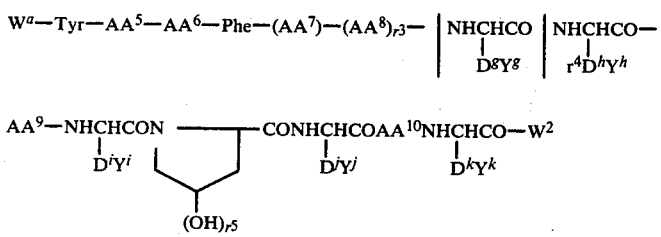

wherein:
AA⁵⁻¹⁰ are hydrophobic amino acids being unsubstituted at the α position or having one substituent which is hydrocarbon or having a single chalcogen atom (O or S) and of from 1 to 8, usually 1 to 6, more usually 1 to 4 carbon atoms, when aliphatic and 6 to 8 carbon atoms when aromatic; being normally aliphatic, usually free of aliphatic unsaturation, either straight chain or branched, the chalcogen atom bonded solely to carbon and hydrogen, usually carbon, particularly AA⁷ may be alkoxy or alkylthioalkylene of from 2 to 6, usually 3 to 4 carbon atoms;

the preferred amino acids which come within the above definition include glycine, alanine, valine, leucine, isoleucine and methionine. Less preferred amino acids include phenylalanine, serine, and threonine. That is, those amino acids which are substantially neutral; one or more of AA⁵⁻¹⁰ may be of the D-configuration, for example AA⁵⁻⁶;

$D^g$ to $D^k$ are alkylene of from 2 to 6, usually 2 to 4 carbon atoms, more usually 3 to 4 carbon atoms.

$Y^g$ to $Y^k$ are amino or guanidinyl, either as the amine or its salt;

$W^a$ and $W^2$ have been defined previously; and $r^{3-5}$ are 0 or 1, preferably $r^3$ being 0, and $r^4$ being 1, and $r^5$ being 0.

It should be understood, that one or more of the basic amino acids may be substituted by histidine, tryptophan or other amino acid, natural or unnatural, which would provide some or equivalent basicity to the naturally occurring basic amino acids, lysine and arginine. In addition, one or more other amino acids may be substituted for the hydrophobic amino acids, such as cysteine, threonine, or serine. However, since the presence of the hydroxyl and mercapto functionalities are believed to be unnecessary, the employment of the hydrocarbon group is preferred. Finally, one or more peptide bonds may be modified, particularly the peptide bond of a basic amino acid to a non-basic amino acid, where the basic amino acid follows a basic amino acid in going from the N-terminus. Modification could also include reducing the peptide link to a methyleneamine or similar link.

Of particular interest is the polypeptide of the formula wherein:

AA⁵ is glycine, D- or L-analine;
AA⁶ is glycine;
AA⁷ is leucine or methionine;
$r^3$ and $r^5$ are 0;
$r^4$ is 1;
$D^g$, $D^h$, and $D^i$ are trimethylene and $Y^g$, $Y^h$, and $Y^i$ are guanidinyl;
$D^j$ and $D^k$ are tetramethylene and $Y^j$ and $Y^k$ are amino;
AA¹⁰ is leucine;
$W^a$ is hydrogen; and
$W^2$ is hydroxyl or amino.

The subject compositions because of their high basicity may be combined with polypeptides which have reciprocal amino acids, that is, aspartic or glutamic acid. The acidic amino acids would be linked to hydrophobic amino acids and the resulting oligopeptide acid groups appropriately spaced with hydrophobic amino acids to associate with the basic groups of the subject oligopeptides. Such compositions could be used in combination with the subject oligopeptides, for example, a sextet combined with an enkephalin and the oligopeptide designates as W. Alternatively the acidic oligopeptide could be linked by a peptide link at the C-terminus, particularly through 1 to 2 basic amino groups.

The complementary acidic oligopeptide will for the most part have the following formula:

wherein:
- $AA^{11-13}$ are glycine or aliphatically substituted amino acids, having alkyl groups from 1 to 6, usually one 1 three 3 atoms at the α position;
- $R^{j-n}$ are alkylene of from 1 to 2 carbon atoms, desirably the number of carbon atoms of the complementary D and R groups being a total of 6, that is, lysine would be complementary to aspartic acid, while arginine would be complementary to glutamic acid; and
- $r^{6-8}$ are 0 or 1.

The subject compositions may be readily prepared by conventional techniques, for example, a solid state technique performed on a resin support. See Steward and Young, Solid-Phase Peptide Synthesis, W. H. Freeman Co., San Francisco (1969) and Merrifield, J. Am. Chem. Soc. 85 2149–2154 (1963). Conveniently, the oligopeptides may be synthesized automatically employing a Beckman Model 990 Peptide Synthesizer, available from the Spinco Division of Beckman Instruments, Inc., described in Instruction Manual No. SY-IM-2, December 1972.

The compounds of the subject invention, particularly the trideca- and higher oligopeptides may be used for preparing antisera for use in immunoassays employing labeled oligopeptides. Conveniently, the oligopeptides may be conjugated to an antigen by means of dialdehydes, particularly of from 4 to 6 carbon atoms and aliphatic. The oligopeptides may be labeled with a variety of labels which are conventionally employed in the literature. Illustrative labels which may be found in patents, are radioactive tags, such as $^{125}I$ or $^{3}H$, enzymes, fluorescers or the like. See for example U.S. Pat. Nos. 3,766,162, 3,817,837 and 3,998,943, the appropriate portions of which, describing the labeling and immunoassay, are incorporated herein by reference.

The following examples are offered by way of illustration and not by way of limitation.

EXPERIMENTAL (All temperatures not otherwise indicated are in centigrade. All percents and parts not otherwise indicated are by weight except for mixtures of liquids which are by volume.) The following composition was isolated as follows.

H-tyr-gly-gly-phe-leu-arg-arg-ile-arg-pro-lys-leu-lys-OH

The compound is referred to as dynorphin.

Purification and partial sequencing of porcine dynorphin

Starting material was 100 g MSH concentrate, the second oxycellulose adsorbate in commercial ACTH production from procine pituitary glands (Schally et al (1962) Endocrinology 71, 164). The initial steps, with 25 g batches, have been described in Lowney et al (1979) Life Sci. 24, 2377: extraction and back-extraction with butanol; separation from β-endorphin on Bio-Gel P6; preparative reversed-phase HPLC on $C_{18}$ columns, first with a methanol gradient in trifluoroacetic acid (TFA), then with an acetonitrile gradient in Tris buffer at neutrality, followed by elution of the active material with TFA. Every step was monitored by assay on the guinea pig ileum myenteric plexus-longitudinal muscle preparation. Kosterlitz & Waterfled (1975) Ann. Rev. Pharmacol. 15, 29; Schulz & Goldstein (1973) Brit. J. Pharmacol. 48, 655.

Pooled material from four batches, obtained as above, was loaded on a Bio-Gel column (P-6 and P-4, 4:1; 1.5×90 cm) in 0.1 M $(NH_4)_2CO_3$, pH 8.7. Fractions (1.7 ml, 15 min) were tested for activity in the bioassay. The peak of slow-reversing activity (Lowney, supra) (fractions 65–75) was lyophilized, then further purified on CM-Sephadex (0.9×30 cm) equilibrated with 12.5 mM sodium borate buffer, pH 11.0. The material was eluted with a 106 ml linear gradient from the starting buffer to 0.1 M phosphate buffer, pH 12.0. Fractions (2.0 ml, 15 min) were collected and assayed. Slow-reversing activity emerged between 94 and 106 ml. The two peak tubes, containing 50% of the activity, were pooled and desalted on Bio-Gel P-2 (1.5×90 cm) in n-butanol:acetic acid:water (2:1:4).

Finally, the desalted material was subjected to reverse phase chromatography on HPLC ($C_{18}$ column) using a 10–50% acetonitrile gradient in 5 mM TFA. The peak of biologic activity had no measurable absorbance at 280 nm. A rough estimate of quantity from absorbance at 225 and 215 nm indicated the presence of only a few micrograms of peptide, but the activity in the bioassay was equivalent to 334 nmoles of normorphine (range 189–525 in four tissue strips).

One-third of the material was dansylated, applied to a silica gel 60 H (Merck) TLC plate, and developed in methyl acetate:pyridine:methanol (9:7:4). Two fluorescent bands were observed with Rf=0 (band 1) and Rf=0.20 (band 2). Each band was extracted using methanol:pyridine:acetic acid (1:1:1) and demonstrated to be homogeneous by TLC in n-butanol:acetic acid:water (4:1:5, upper phase), with Rf=0.33 (band 1) and Rf=0.51 (band 2). After hydrolysis (6 N HCl, 16 hr, 105° C.), material from each band was examined for dansylated N-terminal residues, using reverse phase HPLC ($C_{18}$ column, 45 min linear gradient, 5 to 50% acetonitrile in 10 mM Tris, pH 7.0, Varian fluorometric detector). Trace amounts of ε-DNS-lys and di-DNS-tyr were detected in the hydrolysate from Band 1. The Band 2 hydrolysate revealed only ε-DNS-lys.

Microsequencing of the peptide material was performed by the spinning cup procedure. Hunkapiller & Hood (1978) Biochemistry 17, 2124. An unambiguous sequence was obtained with one-third of the total material, for 13 residues. The amount of peptide, estimated from the first few cycles, was about 400 pmoles, and thus, the potency in the bioassay was approximately ⅓ of 334/0.400, or 267 times that of normorphine. Presence of a blocked contaminant was confirmed in the composition data, which gave distinctly non-integer ratios.

The tridecapeptide was synthesized with a sequence corresponding to porcine dynorphin-(1–13): H-tyr-gly-gly-phe-leu-arg-arg-ile-arg-pro-lys-leu-lys-OH. Purity was shown to be greater than 98% in the following systems: (a) n-butanol:pyridine:acetic acid:water (42:24:4:30), cellulose plate, Rf=0.54; (b) n-butanol:a- cetic acid-water (4:1:5 upper phase), silica gel plate, Rf=0.05; (c) formic-acetic acid, pH 1.9, electrophoresis, 22 V/cm, 1 hr, Whatman 3MM, Rf=1.40 with reference to picric acid. Composition was confirmed by amino acid analysis. The sequence of the synthetic tridecapeptide was also confirmed by analysis on the spinning-cup sequenator.

Two related peptides (referred to here as "register-shift peptides") were also synthesized. These were the des-arg[6] dodecapeptide from dynorphin-(1-13), and the gly[6] tetradecapeptide derivative, in which gly is inserted between leu[5] and arg[6]. Standards of purity were the same as noted above for the tridecapeptide.

Biologic activity

Dilutions for all bioassays were carried out in methanol:0.1 N HCl (1:1, v/v), dilutions for radioimmunoassays in 50 mM phosphate buffer, pH 7.4, containing 50 mM NaCl, 0.1% bovine serum albumin, and 0.5% Triton X-100.

The guinea pig ileum myenteric plexus-longitudinal muscle preparation was used as described in Kosterlitz et al, supra, and Schulz & Goldstein, supra. A determination of IC50 was done by bracketing, with at least one concentration giving more than, and one giving less than 50% inhibition of the electrically stimulated twitch, and interpolating on a log concentration-percent inhibition plot. Geometric means of IC50 values from several muscle strips were obtained, with standard errors in log units. $K_d$ values for naloxone as an antagonist were determined from the ratio of IC50 values in the presence and absence of a fixed naloxone concentration. The mouse vas deferens was used as described in Hughes at al (1975) Brit. J. Pharmacol. 53, 371. IC50 and naloxone $K_d$ values were determined as above. In both bioassays, volumes of methanol-HCl solvent up to 20 μl in the 5-ml tissue bath were without effect.

The radioreceptor binding assay used well washed rat brain membranes that had been incubated for 30 min at 37° with 100 mM NaCl to remove bound endogenous ligands. Blume (1978) Proc. Natl. Acad. Sci. 75, 1713. Several radioligands (1 nM final concentration) and competing ligands were tested. Competing ligands were added to the membrane suspension in Tris buffer, pH 7.4 at 23°, and radioligand was added immediately thereafter. Assay volume was 500 μl. After incubation (1 h, 23°), the mixture was chilled, filtered, washed twice, and counted. Displacement of radioligand by levallorphan (1 μM final concentration) was taken as measure of stereospecific saturable binding; this was usually about 70% of total binding. The (+) isomer dextrallorphan was without effect under these conditions. Methanol-HCl solvent, present in all incubation tubes in a volume of 5 μl, had no effect on control binding.

[125]-I-dynorphin-(1-13) was prepared by a modification of the method of Hunter and Greenwood, (1962), Nature 194, 495, and separated from unreacted iodide on a Sephadex G-15 column with 0.1% bovine serum albumin in 0.25 M acetic acid. Peptide degradation in vivo and by rat brain membranes was estimated by a shift in the radioactivity peak on a Bio-Gel P-2 column (1.2×41 cm) using n-butanol:acetic acid:water (2:1:4).

For radioimmunoassay, two different antisera were used, raised to leucine-enkephalin in rabbits. See Watson et al (1979) Endorphins in Mental Health Research eds. Usdin, Bunney & Kline (Oxford University Press, New York). Antisera were used at final dilutions required to bind about 30% of [125]-I-leucine-enkephalin in the absence of a competing ligand. This radioligand was prepared by the chloramine-T method (Hunter and Greenwood (1962) Nature 194, 495) and purified on DEAE-Sephadex. In each tube, 100 μl of peptide to be assayed was added to 100 μl of diluted antiserum, and the mixture was incubated 48 h at 4°. Then 100 μl of radioligand (approx. 5000 cpm) was added, and incubation was continued another 24 h. The incubation was terminated by adding 100 μl of normal rabbit plasma and 1.5 ml of 15.8% polyethylene glycol. After 10 min on ice, the mixture was centrifuged 15 min at 4000×g, the supernatent solution was aspirated, and the tube containing precipitate was placed in a gamma counter.

Table 1

Effects of dynorphin-(1-13) in two bioassays. IC50 values were obtained from assays spanning the 50% inhibition response, plotted on log dose-percent inhibition plots. Naloxone $K_d$ is the apparent dissociation constant of the antagonist, computed from the equation $K_d = D/(D.R.-1)$, derived from the mass law for competitive antagonism, where C=concentration of naloxone (here 100 nM), and D.R. =dose ratio of agonist, the ratio of IC50 doses in the presence and absence of the antagonist. The same procedures were followed with the mouse vas deferens. IC50 values are geometric means, with standard errors in log units, number of tissue preparations in parentheses. $K_d$ determinations were based on four tissue preparations. RX-1 is des-arg[6]-dynorphin-(1-13); RS-2 has gly[6] insertion in dynorphin-(1-13).

TABLE 1

| | Guinea pig ileum myenteric-plexus longitudinal muscle preparation | | | Mouse vas deferens | | | Potency in mouse vas deferns potency in guinea pig ileum |
|---|---|---|---|---|---|---|---|
| | IC50 (nM) | s.e.m. (log units) | Naloxone $K_d \pm$ s.e.m. (nM) | IC50 (nM) | s.e.m. (log units) | Naloxone $K_d \pm$ s.e.m. (nM) | |
| Dynorphin-(1-13) | 0.63 | 0.07 (18) | 33 ± 4 | 7.5 | 0.06 (8) | 120 ± 49 | 0.08 |
| Leucine-enkephalin | 460 | 0.09 (18) | 2.5 ± 0.1 | 23 | 0.10 (8) | 40 ± 10 | 20. |
| $\beta_c$-endorphin | 34 | 0.11 (4) | — | 24,21 | — (2) | — | 1.5 |
| Normorphine | 120 | 0.06 (18) | 2.1 ± 0.2 | 230 | 0.11 (8) | 12 ± 6 | 0.52 |
| RS-1 | 7.5 | 0.07 (7) | 20 ± 4 | | | | |
| RS-2 | 4.8 | 0.08 (8) | 15 ± 4 | | | | |

Table 2

Effects of dynorphin-(1-13) in the radioreceptor binding assay. Washed membranes from rat brain homogenate, 1 h incubation at 23°. Data are IC50 values (nM) from complete log dose-inhibition curves for inhibition of stereospecific binding of the various radioligands. Total stereospecific binding was determined with levallorphan (1 μm) as competing ligand; dextrallorphan (1 μM) was without effect. DADLE=D-ala²-D-leu⁵-enkephalin. DHM=dihydromorphine.

| Competing ligand | Radioligand | | | |
|---|---|---|---|---|
| | ³H—naloxone | | ³H—DADLE | ³H—DHM |
| | −Na | +Na | | |
| Dynorphin-(1-13) | 14,22 | 145,165 | 43$^a$ | 16 |
| Leucine-enkephalin | 6000$^a$ | — | 400$^a$ | 2100$^a$ |
| $\beta_c$-endorphin | 1.4,1.9 | 34,40 | 2.1 | 1.8 |
| Normorphine | 21 | 260 | 23$^a$ | 5.0 |

$^a$These slopes were unusually shallow; all other slopes were compatible with the theoretical slope expected from the mass law equation.

The natural and synthetic dynorphin is found to be substantially more active than the enkephalins and β-endophin in the guinea pig ileum test. The dynorphin is found to be about 1000x greater potency than leu-enkephalin, about 350x greater potency than normorphine and about 30x more potent than β-endorphin. The compound is relatively resistant to treatment with cyanogen bromide and has long persistence in the guinea pig ileum test, unlike β-endorphin. The molecular weight is found to be about 1750.

Alternative illustrative sequences include:

Tyr-gly-gly-phe-leu-arg-arg-ile-arg-pro-lys-leu-lys-lys-OH

Tyr-D-ala-gly-phe-lys-lys-ile-arg-pro-lys-leu-lys-NH₂

Tyr-D-ala-gly-phe-met-arg-arg-ile-arg-pro-lys-leu-lys-NH₂

Tyr-gly-gly-phe-leu-arg-D-arg-ile-lys-pro-lys-leu-lys-OH

The subject analgesic compositions by virtue of their interaction with opioid receptor sites can provide a wide range of physiological effects, such as mood altering effects, analgesia, muscle relaxation and blood flow regulation. In vivo analgesic effect related to the subject in vitro tests is well established as demonstrated by studies reported in Walker et al., Science, 196, 85 (1977). The compositions of this invention can be administered to a mammalian host e.g. domestic animals, and man, in the same manner as other opioid agonists e.g. morphine, are administered. For the most part, the administered dosage will range from about 0.05 to 40 mg, more usually about 0.5 to 20 mg per 70 kg body weight.

The drug may be administered neat, admixed with physiologically acceptable powders or dissolved in physiologically acceptable liquid e.g. water or aqueous ethanol, usually having not more than about 60 volume percent ethanol. The drug may be administered orally, by inhalation, or parenterally e.g. subcutaneously, intravenously or intramuscularly. Concentration of the drug in admixtures or solutions will generally range from about 0.5 to 50 weight percent, usually from about 1 to 30 weight percent.

The subject drugs may be used individually or in combination with other drugs, normally employed in conjunction with analgesics. These drugs include aspirin and L-dopa.

When administered as a solid, the subject drugs may be administered as pills, capsules, powders, or the like.

The subject dynorphin was used for the development of immunoassays, illustrated particularly by a radioimmunoassay. For carrying out the immunoassay, it is necessary to prepare antigens which specifically recognize the oligopeptide, in this case dynorphin. To prepare antigen conjugates, thyroglobulin was conjugated to synthetic dynorphin (1-13). The procedure for preparing the antigen conjugate, injecting the antigen conjugate into animals and isolating the antisera is described as follows.

Synthetic dynorphin (1-13) (3.25 μmoles, 5.2 mg) was dissolved in 2 ml of 100 mM sodium phosphate buffer at neutrality. To the mixture was added with agitation 10⁵cpm of ¹²⁵I-dynorphin to serve as a tracer. After addition of the tracer, 26 mg of thyroglobulin (bovine type 1, Sigma) was added and the mixture cooled in an ice-bath after the thyroglobulin dissolved. A 1:100 dilution with cold water of glutaraldehyde (Sigma, Grade 1, 25% aqueous solution) (1 ml) was added dropwise with stirring in a cold room at 4° and agitation continued for 30 min., followed by warming to room temperature and continuing the stirring for 3 hrs.

Using a Spectropore dialysis membrane (6,000–8,000 dalton cut-off), the reaction mixture was dialyzed against 0.1 M sodium phosphate buffer, pH7.4, containing 0.45% NaCl for 5 hrs. in the cold, followed by dialysis overnight against 0.9% NaCl and then against distilled water (3×5 hrs.).

Based on the coupling efficiency calculated from the cpm of the dialysis bag residue, after lyophilizing, sufficient of the conjugate was employed to provide 50–100 μg of coupled oligopeptide per rabbit. For six rabbits, the dry material was added to 4 ml of 0.9% NaCl, followed by 4 ml of Freund's incomplete adjuvant. The mixture was uniformly dispersed by drawing up and down in a syringe and needle for 30 mins., the mixture divided into six aliquots and approximately 10 to 12 interdermal injections made in a shaved New Zealand White X San Juan hybrid rabbit. Booster injections were made at two week intervals, with a bleeding taken 10 days after the fourth booster shot, 50 ml of blood being removed from the ear artery, allowed to clot, the serum removed and stored frozen.

The tracer dynorphin (1-13) having ¹²⁵I was prepared as follows.

The following reagents were prepared: sodium ¹²⁵I (17 Ci/mgI) in 5 μl batches in 0.1 N sodium hydroxide was diluted with 0.1 M sodium phosphate buffer, pH7.4, to make 1 mCi/25 μl solutions, including the HCl added to neutralize the sodium hydroxide.

Chloramine-T (Sigma) was made 0.5 mg/ml in 0.1 M sodium phosphate buffer, pH7.4.

Sodium metabisulfite, 1 mg/ml in 0.1 M sodium phosphate buffer, pH7.4.

In small borosilicate tubes was added 25 μl dynorphin (equimolar to Na ¹²⁵I), 50 μl Na ¹²⁵I, and 20 μl chloramine-T and the mixture allowed to react at room temperature for 30-45 mins. The reaction was terminated by adding 100 μl of sodium metabisulfite. After washing a Sephadex G-15 column (1.2×35 cm) with 0.25 M acetic acid and 0.1% bovine serum albumin, the reaction mixture was added and eluted with the same solvent, collecting 1 ml fractions at a rate of 0.3 ml/min, collecting a total of 50 fractions. About five tubes around fraction 25 contained most of the peptide.

In order to perform the radioimmunoassay, the following reagents were prepared.

Buffer A: 0.150 M sodium phosphate, pH7.4;

Buffer B, buffer A containing 0.1% bovine serum albumin and 0.1% Triton X-100;

Methanolic HCl: methanol-0.1 N HCl (1:1, v:v).

Antiserum: A 1:10 dilution of the antiserum in 50 mM sodium phosphate buffer, pH7.4, containing 50 mM NaCl was diluted 1:10$^4$ with buffer B;

Dynorphin (1–13) standard: Standards were prepared by taking 10 μl of a 10 mM stock solution in water and adding 990 μl of methanolic HCl to make a 100 mM dynorphin solution followed by 1:100 dilutions to provide the desired series.

$^{125}$I-dynorphin (1–13) trace: The trace stored in 0.25 M acetic acid containing 0.1% BSA was diluted to about 5,000 cpm/100 μl with buffer B.

The procedure for the assay was as follows: All solutions were in ice at the outset and all operations were carried out in ice. In a 13×100 mM borosilicate glass tube was added in the following order 100 μl of dynorphin (1–13) standard or test sample in methanolic HCl; 100 μl of the antiserum dilution; and 100 μl of the trace, followed by incubation at 0°–4° for 24 hrs. Incubation was terminated with a charcoal mixture prepared by mixing 3 g Norit A, 0.3 g dextran, 15 ml horse serum and the mixture brought to 100 ml with buffer A and mixed for 10 min in a cold room before use. To each incubation tube was added 1 ml of a charcoal mixture, the mixture vortexed followed by incubation for 5 min in a cold room and then centifuged at 5000×g for 15 min in a Beckman Model J6B (4200 rpm). To a 13×100 mm borosilicate glass tube was transferred 850 μl of the supernatant and the tube counted for 5 min in a gamma counter. Since after addition of charcoal, the total volume was 1300 μl, and only 850 μl was counted, the total number of counts is multiplied by 1300/850 to obtain the total amount of bound dynorphin.

The following table indicates the results obtained from the assay.

TABLE

| B/Bo* | Moles Dynorphin per Assay Tube |
|---|---|
| 100 | 1 × 10$^{-16}$ |
| 100 | 5 × 10$^{-16}$ |
| 85 | 1 × 10$^{-15}$ |
| 75 | 5 × 10$^{-15}$ |
| 45 | 1 × 10$^{-14}$ |
| 30 | 5 × 10$^{-14}$ |
| 15 | 1 × 10$^{-13}$ |
| 5 | 5 × 10$^{-13}$ |

*B/Bo—the total number of counts calculated for the observed value divided by the total number of counts in the absence of dynorphin competitor (methanolic HCl substituted for the standard)

When fragments of dynorphin were substituted for dynorphin, namely leu-enkephalin, dynorphin (6–13) and N-acetyl dynorphin (6–13), there was no evidence of any cross reactivity with dynorphin.

Noteworthy, was the fact that efforts to establish the presence of any antibodies which would bind specifically to leucine enkephalin failed, since even at an antiserum concentration as high as 1:10 dilution, neither iodinated nor tritiated leucine enkephalin was bound by the antiserum.

Based on the above data, it is also evident, that the antiserum recognizes the area of the dynorphin (1–13) at about the 5–6 amino acids from the N-terminus. Thus, the subject antiserum is specific for dynorphin (1–13) and is able to distinguish leu-enkephalin.

It is evident from the above results, that the subject compositions can be used to prepare a sensitive assay for a natural analgesic, by the preparation of a specific, strongly binding antiserum and a labeled analog of the dynorphin. Besides employing a radioactive label, other labels may be employed which include fluorescers, enzymes, or other convenient label.

The subject opioid activity containing compounds also find use as standards in testing for binding to opioid receptor sites for other drugs and investigating the secondary and tertiary structural characteristics of opioid receptor binding sites. Thus, the subject products find use as a pharmaceutical product, in both research and commercial applications.

In addition the subject compounds can be used as precursors to potentiate the binding properties of known analgesic compounds.

The subject invention greatly extends the ability to achieve analgesic effects by employing natural products or modified natural products. In this way, pain can be alleviated with minimal interference with natural processes, without introduction of undersirable side products and without causing side effects. Furthermore, by allowing for further understanding of the opioid binding site, the subject compositions offer directions to new drugs or other means to provide opiate antagonists or agonists. By potentiating the opioid compounds, lower concentrations will be required, so as to potentially reduce side effects.

Although the foregoing invention has been described in some detail by way of illustration and example for purposes of clarity of understanding, it will be obvious that certain changes and modifications may be practiced within the scope of the appended claims.

What is claimed is:

1. Dynorphin substantially free of products from the pituitary gland.

2. A compound of the formula

H-tyr-gly-gly-phe-leu-arg-arg-ile-arg-pro-lys-leu-lys-W$^3$, where W$^3$ is hydroxyl or amino.

3. A compound of the formula

H-tyr-gly-gly-phe-leu-arg-ile-arg-pro-lys-leu-lys-W$^3$, where W$^3$ is hydroxyl or amino.

4. A compound of the formula

H-tyr-gly-gly-phe-leu-gly-arg-arg-ile-arg-pro-lys-leu-lys-W$^3$, where W$^3$ is hydroxyl or amino.

5. A compound of the formula

Tyr-gly-gly-phe-leu-(arg or lys)$_{r4}$-(arg or lys)-ile-arg-(pro or HOpro)-(arg or lys)-leu-(arg or lys)-W$^2$ wherein:

r$^4$ is 0 or one; and

W$^2$ is hydroxyl or amino.

6. A method for inducing analgesia in a mammalian host which comprises administering to said host in an amount sufficient to induce analgesia a compound according to any of claims 2, 3, 4 or 1.

* * * * *